US00PP17325P2

(12) United States Plant Patent
Brown, Jr.

(10) Patent No.: US PP17,325 P2
(45) Date of Patent: Dec. 26, 2006

(54) ***PERSICARIA* PLANT NAMED 'CHOCOLATE DRAGON'**

(50) Latin Name: *Persicaria microcephala*
Varietal Denomination: Chocolate Dragon

(75) Inventor: Kenneth E. Brown, Jr., Tigard, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 2 days.

(21) Appl. No.: 11/166,542

(22) Filed: Jun. 24, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarrquist Sparkman LLP

(57) ABSTRACT

A new and distinct cultivar of *Persicaria* plant characterized by its compact habit and multicolored leaves exhibiting a two-toned effect with the younger leaves dark purple brown and patterned while the older leaves are green and patterned.

1 Drawing Sheet

Botanical denomination: *Persicaria microcephala.*
Variety designation: 'Chocolate Dragon'.

BACKGROUND OF THE INVENTION

The present invention relates to a new and distinct cultivar of an herbaceous perennial of the genus, *Persicaria*, and known by the cultivar name of 'Chocolate Dragon'. The genus *Persicaria* is a member of the family Polygonaceae.

The new cultivar is a seedling of *Persicaria microcephala* 'Red Dragon' (U.S Plant Pat. No. 12,062). It was found among hundreds of seedlings in a neighborhood backyard.

SUMMARY OF THE INVENTION

This new cultivar is characterized by:

1) Striking leaves that are purple brown when young and mature to being brown with a silvery olive chevron and then become bright green with a dark basal blotch. This gives the plant a two toned effect.
2) Low, mounding habit.

The new variety has been reproduced only by asexual propagation (cutting and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
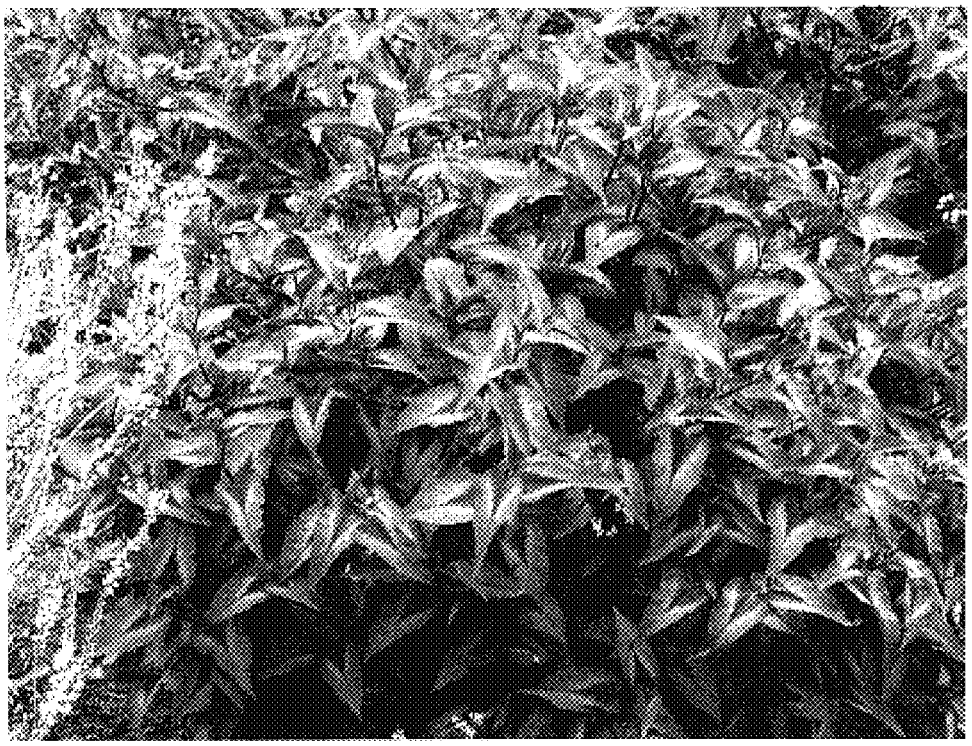
FIG. 1 shows a two-year-old plant growing in the garden in Canby, Oreg.
Figure 2:
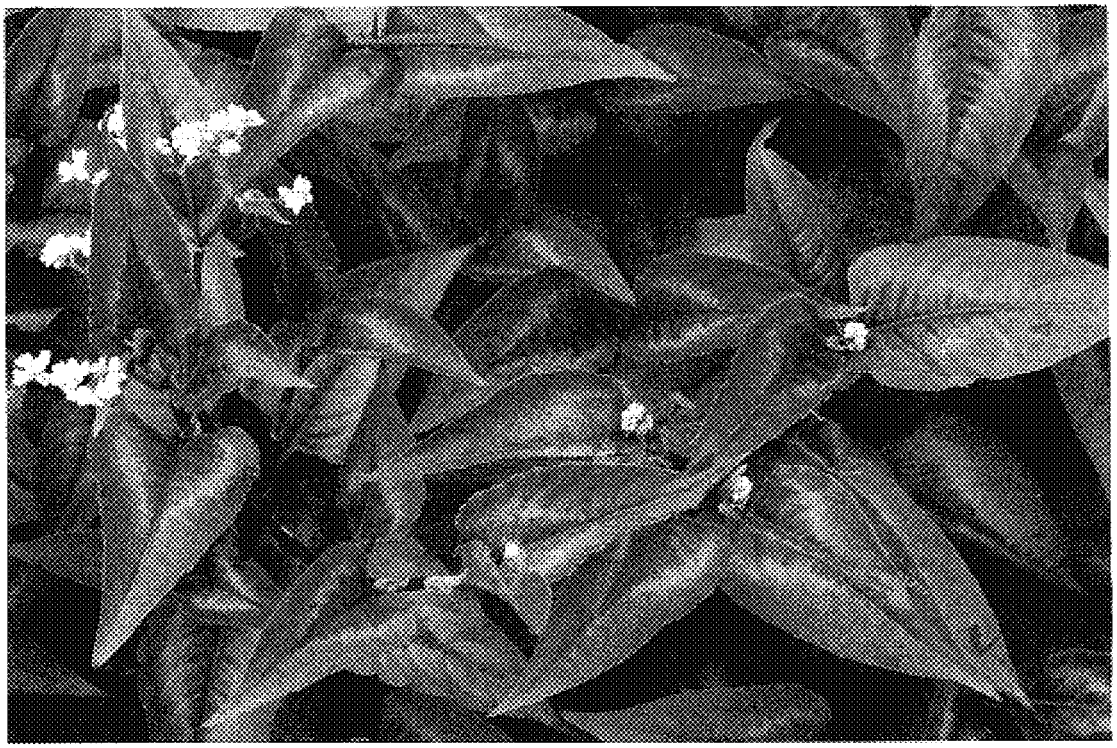
FIG. 2 shows a close up.

The following is a detailed description of the new cultivar based on observations of two-year-old specimens growing in late September in the ground in full sun under typical outdoor conditions in the trial fields in Canby, Oreg. Canby is in Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical name: *Persicaria microcephala.*
Cultivar name: 'Chocolate Dragon'.
Plant:
- *Type.*—Herbaceous perennial.
- *Form.*—Mound.
- *Hardiness.*—USDA Zones 5 to 9.
- *Size.*—80 cm tall and 100 cm wide.
- *Habit.*—Clumping.

Stem:
- *Type.*—Succulent, with swollen nodes and sheath-like membranous stipules, well branched.
- *Diameter.*—4.5 mm above the third node down from the tip, 8 mm at plant base.
- *Internode spacing.*—4 to 10 cm.
- *Surface.*—Glabrous.
- *Color.*—Dark purple red. Greyed Purple 185A.

Leaf:
- *Type.*—Simple.
- *Arrangement.*—Alternate.
- *Shape.*—Ovate.
- *Venation.*—Pinnate.
- *Margins.*—Entire.
- *Apex.*—Accuminate to cuspidate.
- *Base.*—Truncate.
- *Blade size.*—5.6 to 7.4 cm long and 3 to 3.7 cm wide.
- *Surface texture.*—Sparsely pubescent.
- *Petiole size.*—7 to 10 mm and clasping at base and 2 mm wide.

*Petiole and major vein color.*—Greyed Purple 185A to 187C.

*Leaf color.*—Variable depending on the light intensity. New leaves topside: Between Brown 200A and Greyed Purple 187A with an even darker, triangle-shaped basal spot, Greyed Purple 187A and a light v-shaped chevron at edge of spot, Grey 201D blended with Brown 200A. New leaves bottom side: Closest to Greyed Orange 177A. Full size dark leaf topside: Khaki or grey greenish brown (closest to Greyed Green 197A but darker and browner) with a lighter chevron (Greyed Yellow 160 but duller) and a darker spot at the base, Brown 200A. Mature leaves bottom side: Between Greyed Orange 177A and Greyed Green 197A. Older leaves topside: Green 147A with lighter at chevron and spot is khaki (closest to Greyed Green 197A but darker and browner). Older leaves bottom side: Yellow Green 147B.

Inflorescence:

*Type.*—Terminal compound corymbs.

*Number of flowers.*—50 per corymb.

*Corymb size.*—Variable. 3.5 cm wide and 3 cm deep without peduncle.

*Peduncle description.*—2.5 to 3 cm long and 2 mm wide, glabrous to sparsely pubescent, Greyed Red 181A.

*Pedicel.*—Greyed Red 181C, sparsely pubescent.

*Bloom period.*—August to frost in Canby, Oreg.

Flower bud:

*Size.*—3 mm long and 2 mm wide.

*Description.*—Ovoid.

*Color.*—Light pink, Red 54C with White 155D tips.

Flower:

*Type.*—Perfect, actinomorphic.

*Shape.*—Campanulate.

*Size.*—3 mm deep and 3 mm wide.

*Petal description.*—5 overlapping lobes, margins entire, apex acute, waxy and thick surface texture.

*Petal color.*—White 155D at tips and light pink, Red 56D to Red 54C at base. The same on both sides.

*Calyx.*—Scarious, 0.5 mm deep and wide, margins entire, apex acute.

*Calyx color.*—Greyed Orange 177D.

*Stamen number.*—8.

*Filaments.*—White 155D.

*Anther color.*—Purple 79C.

*Pollen color.*—White 155D.

*Pistil color.*—White 155D.

*Pistil.*—Three branched style, 3 capitulate stigmas.

*Fragrance.*—None.

*Lastingness.*—Each corymb blooms for about 3 weeks on the plant.

Fruit: Never seen.

Seed: Never seen.

Disease and pest resistance and tolerance: *Persicaria* as a genus are susceptible to aphids, slugs and snails. No insect or diseases have been noted on *Persicaria* 'Chocolate Dragon'.

Comparison to Similar *Persicaria*

Compared to its parent *Persicaria* 'Red Dragon' (U.S. Pat. No. 12,062), *Persicaria* 'Chocolate Dragon' is much shorter and more compact with smaller leaves. While *Persicaria* 'Red Dragon' is sprawling and weaving in its habit, this new variety forms a clean mound. Its leaves have a two toned effect for the whole plant with the dark new leaves and the green older leaves. *Persicaria* 'Red Dragon' has less contrast but more pattern. Both have red purple stems.

I claim:

1. A new and distinct hybrid of *Persicaria* plant as herein illustrated and described.

* * * * *